US011904090B2

(12) United States Patent
Garthaffner et al.

(10) Patent No.: US 11,904,090 B2
(45) Date of Patent: *Feb. 20, 2024

(54) ELECTRONIC VAPING DEVICE

(71) Applicant: Altria Client Services LLC, Richmond, VA (US)

(72) Inventors: Travis Martin Garthaffner, Chesterfield, VA (US); Peter J. Lipowicz, Midlothian, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/154,965

(22) Filed: Jan. 16, 2023

(65) Prior Publication Data
US 2023/0149645 A1 May 18, 2023

Related U.S. Application Data

(63) Continuation of application No. 16/673,169, filed on Nov. 4, 2019, now Pat. No. 11,559,638, which is a (Continued)

(51) Int. Cl.
*A61M 15/06* (2006.01)
*H05B 3/26* (2006.01)
(Continued)

(52) U.S. Cl.
CPC .............. *A61M 15/06* (2013.01); *A24F 40/42* (2020.01); *A24F 40/44* (2020.01); *A24F 40/46* (2020.01);
(Continued)

(58) Field of Classification Search
CPC ....... A24F 47/008; A24F 40/42; A61M 15/06; A61M 11/042
See application file for complete search history.

(56) References Cited

U.S. PATENT DOCUMENTS 8,528,569 B1  9/2013 Newton
8,910,640 B2  12/2014 Sears et al.
(Continued)

FOREIGN PATENT DOCUMENTS

CN  101090860 A  12/2007
CN  103504478 A  1/2014
(Continued)

OTHER PUBLICATIONS

Notice of Allowance dated Apr. 6, 2023 issued in related Japanese patent application No. 2018-553350.
(Continued)

*Primary Examiner* — Neil Abrams
(74) *Attorney, Agent, or Firm* — Harness, Dickey & Pierce, P.L.C.

(57) ABSTRACT

A cartridge of an electronic vaping device includes a housing extending in a longitudinal direction. The housing includes a sidewall, a transverse wall at the first end of the sidewall, and an inner tube integrally formed with the housing. The sidewall is generally cylindrical and a first end and a second end. The transverse wall includes at least one outlet therein. The inner tube extends in the longitudinal direction. The inner tube is concentrically positioned with respect to the sidewall. The inner tube communicates with the at least one outlet. The cartridge also includes a reservoir between the sidewall and the inner tube. The reservoir is configured to contain a pre-vapor formulation.

16 Claims, 4 Drawing Sheets

Related U.S. Application Data continuation of application No. 15/095,505, filed on Apr. 11, 2016, now Pat. No. 10,463,076.

(51) Int. Cl.

| | |
|---|---|
| *A61M 11/04* | (2006.01) |
| *A24F 40/42* | (2020.01) |
| *A24F 40/44* | (2020.01) |
| *A24F 40/46* | (2020.01) |
| *A61M 16/00* | (2006.01) |
| *A24F 40/10* | (2020.01) |

(52) U.S. Cl.
CPC .......... *A61M 11/042* (2014.02); *H05B 3/265* (2013.01); *A24F 40/10* (2020.01); *A61M 2016/0021* (2013.01); *A61M 2016/0027* (2013.01); *A61M 2205/3653* (2013.01); *A61M 2205/8206* (2013.01); *H05B 2203/021* (2013.01)

(56) References Cited

U.S. PATENT DOCUMENTS

| | | | |
|---|---|---|---|
| 9,004,073 B2 | 4/2015 | Tucker et al. | |
| 9,078,473 B2 | 7/2015 | Worm et al. | |
| 9,888,719 B2 | 2/2018 | Cadieux et al. | |
| 10,463,076 B2* | 11/2019 | Garthaffner | A24F 40/44 |
| 10,660,367 B2* | 5/2020 | Li | F16K 15/025 |
| 11,559,638 B2* | 1/2023 | Garthaffner | A24F 40/42 |
| 2012/0234315 A1 | 9/2012 | Li et al. | |
| 2013/0081642 A1 | 4/2013 | Safari | |
| 2013/0192620 A1 | 8/2013 | Tucker et al. | |
| 2013/0213419 A1 | 8/2013 | Tucker et al. | |
| 2013/0333700 A1 | 12/2013 | Buchberger | |
| 2014/0000638 A1 | 1/2014 | Sebastian et al. | |
| 2014/0006924 A1 | 1/2014 | Tsolis | |
| 2014/0016716 A1 | 1/2014 | Hum et al. | |
| 2014/0041655 A1 | 2/2014 | Barron et al. | |
| 2014/0076310 A1 | 3/2014 | Newton | |
| 2014/0109921 A1 | 4/2014 | Chen | |
| 2014/0216450 A1 | 8/2014 | Liu | |
| 2014/0261408 A1 | 9/2014 | DePiano et al. | |
| 2014/0261486 A1 | 9/2014 | Potter et al. | |
| 2014/0373833 A1 | 12/2014 | Liu | |
| 2014/0376895 A1 | 12/2014 | Han | |
| 2015/0027457 A1 | 1/2015 | Janardhan et al. | |
| 2015/0083147 A1 | 3/2015 | Schiff et al. | |
| 2015/0208731 A1 | 7/2015 | Malamud et al. | |
| 2015/0245669 A1 | 9/2015 | Cadieux et al. | |
| 2016/0058073 A1 | 3/2016 | Chen | |
| 2016/0095357 A1 | 4/2016 | Burton | |
| 2016/0157525 A1 | 6/2016 | Tucker et al. | |

FOREIGN PATENT DOCUMENTS

| | | |
|---|---|---|
| CN | 203457807 U | 3/2014 |
| CN | 203555166 U | 4/2014 |
| CN | 103987285 A | 8/2014 |
| CN | 204070518 U | 1/2015 |
| CN | 104582513 A | 4/2015 |
| CN | 104797150 A | 7/2015 |
| CN | 204466899 U | 7/2015 |
| CN | 204742628 U | 11/2015 |
| CN | 105208882 A | 12/2015 |
| CN | 204907931 U | 12/2015 |
| CN | 105394816 A | 3/2016 |
| CN | 105407748 A | 3/2016 |
| EA | 019736 B1 | 5/2014 |
| EP | 2946678 A1 | 11/2015 |
| EP | 2967149 A2 | 1/2016 |
| JP | 2015-519054 A | 7/2015 |
| KR | 2013-0133322 A | 12/2013 |
| KR | 10-1610033 B1 | 4/2016 |
| RU | 2509516 C2 | 3/2014 |
| WO | WO-2015/131058 A1 | 9/2015 |
| WO | WO-2016/050246 A1 | 4/2016 |

OTHER PUBLICATIONS

V2 Cigs Ex Blank Tank Cartridges Review—E-Liquid & Wax, 2014, p. 1-5, e-Cigarette Reviewer.com.
International Search Report for corresponding International application No. PCT/EP2017/058634 dated Jun. 19, 2017.
https://www.youtube.com/watch?v-tG1TSze593w&t=176s.
El Mono Vapeador, http://www.elmonovapeador.com/v-core-2-0?age-verified+b26274CA07#prettyPhoto, date Mar. 28, 2019, 1 page.
https://www.youtube.com/watch?v=_HY7nH5Gw1g.
https://www.dhgate.com/product/gs-v-core-ce9-2-0-gs-v-core-wick-head-atomizer/162434511.html#ctabBox Sep. 20, 2018, 3 pages.
Russian Decision to Grant and Search Report for corresponding Application No. 2018139520, dated Jun. 11, 2020.
Chinese Office Action dated Oct. 27, 2020 for corresponding Chinese Application No. 201780018118.9, and English-language translation thereof.
Japanese Office Action dated Feb. 15, 2021 for corresponding Japanese Application No. P2018-553350, and english-language translation thereof.
Chinese Notice of Allowance dated Jul. 13, 2021 for corresponding Chinese Application No. 201780018118.9.
Japanese Office Action dated Nov. 17, 2021 for corresponding Japanese Application No. 2018-553350, and English-language translation thereof.
Japanese Office Action dated Aug. 3, 2022 for corresponding Japanese Application No. 2018-553350, and English-language translation thereof.
Korean Notice of Allowance dated Jul. 26, 2022 for corresponding Korean Application No. 10-2018-7029845, and English-language translation thereof.

* cited by examiner

ELECTRONIC VAPING DEVICE

CROSS-REFERENCE TO RELATED APPLICATION(S)

This application is a continuation application of U.S. application Ser. No. 16/673,169, filed Nov. 4, 2019, which is a continuation application of U.S. application Ser. No. 15/095,505, filed Apr. 11, 2016, the entire content of each of which is incorporated herein by reference.

BACKGROUND

Field

The present disclosure relates to an electronic vaping or e-vaping device configured to deliver a pre-vapor formulation to a vaporizer.

Description of Related Art

An electronic vaping device includes a heater element, which vaporizes a pre-vapor formulation to produce a vapor.

SUMMARY

At least one example embodiment relates to a cartridge of an electronic vaping device.

In at least one example embodiment, a cartridge of an electronic vaping device includes a housing extending in a longitudinal direction. The housing includes a sidewall. The sidewall is generally cylindrical and includes a first end and a second end. The housing also includes a transverse wall at the first end of the sidewall. The transverse wall includes at least one outlet therein. The housing also includes an inner tube integrally formed with the housing. The inner tube extends in the longitudinal direction. The inner tube is concentrically positioned with respect to the sidewall. The inner tube communicates with the at least one outlet. The cartridge also includes a reservoir between the sidewall and the inner tube. The reservoir is configured to contain a pre-vapor formulation.

In at least one example embodiment, the cartridge also includes an end cap configured to be attached to the sidewall of the housing at the second end thereof. The end cap includes an end cap sidewall and an end wall. The end cap sidewall is generally cylindrical. The end cap sidewall has a smaller outer diameter than an inner diameter of the sidewall of the housing. The end cap sidewall is configured to be received in the sidewall of the housing.

In at least one example embodiment, the end cap includes at least one inlet therein. The at least one inlet is in communication with the inner tube. The end cap includes a first orifice and a second orifice extending therethrough.

In at least one example embodiment, the cartridge also includes a wick. The wick includes a first end, a second end, and a central portion. The first end and the second end extend through first orifice and the second orifice. The first end and the second end are configured to contact pre-vapor formulation contained in the reservoir. The central portion extends over the at least one inlet. In at least one example embodiment, the wick is formed of at least one of a cellulosic material, a glass material, glass fibers, and cotton. In at least one example embodiment, the wick may be formed of cellulose filter paper having a thickness ranging from about 0.6 mm to about 1.0 mm.

In at least one example embodiment, the end cap includes a third orifice and fourth orifice that extend through the end cap.

In at least one example embodiment, the cartridge also includes a second wick. The second wick includes a third end, a fourth end, and a second central portion. The third end and the fourth end extend through the third orifice and the fourth orifice. The third end and the fourth end are configured to contact pre-vapor formulation contained in the reservoir. The second central portion overlaps with the first central portion.

In at least one example embodiment, at least one of the wick and the second wick is generally U-shaped.

In at least one example embodiment, the housing is formed of plastic.

In at least one example embodiment, the sidewall has a first outer diameter at the first end and a second outer diameter at the second end. The first outer diameter is larger than the second outer diameter.

At least one example embodiment relates to an electronic vaping device.

In at least one example embodiment, an electronic vaping device includes a cartridge of an electronic vaping device includes a housing extending in a longitudinal direction. The housing includes a sidewall. The sidewall is generally cylindrical and includes a first end and a second end. The housing also includes a transverse wall at the first end of the sidewall. The transverse wall includes at least one outlet therein. The housing also includes an inner tube integrally formed with the housing. The inner tube extends in the longitudinal direction. The inner tube is concentrically positioned with respect to the sidewall. The inner tube communicates with the at least one outlet. The cartridge also includes a reservoir between the sidewall and the inner tube. The reservoir is configured to contain a pre-vapor formulation.

In at least one example embodiment, the electronic vaping device also includes a power supply section. The power supply section includes a second housing extending in the longitudinal direction, a battery in the second housing, and a heater electrically connected to the battery. The second housing is configured to connect with the housing via a connection.

In at least one example embodiment, the power supply section also includes a support configured to support the heater. The support is ceramic.

In at least one example embodiment, the power supply section also includes an insulation sleeve adjacent the support.

In at least one example embodiment, the cartridge includes an end cap configured to be attached to the sidewall of the housing at the second end thereof. The end cap includes an end cap sidewall and an end wall. The end cap sidewall is generally cylindrical. The end cap sidewall has a smaller outer diameter than an inner diameter of the sidewall of the housing. The end cap sidewall is configured to be received in the sidewall of the housing.

In at least one example embodiment, the end cap includes at least one inlet therein. The at least one inlet is in communication with the inner tube. The end cap includes a first orifice and a second orifice extending therethrough.

In at least one example embodiment, the cartridge also includes a wick. The wick includes a first end, a second end, and a central portion. The first end and the second end extend through first orifice and the second orifice. The first end and the second end are configured to contact pre-vapor formulation contained in the reservoir. The central portion extends over the at least one inlet. In at least one example embodiment, the wick is formed of at least one of a cellulosic material, a glass material, glass fibers, and cotton.

In at least one example embodiment, the end cap includes a third orifice and fourth orifice that extend through the end cap.

In at least one example embodiment, the cartridge also includes a second wick. The second wick includes a third end, a fourth end, and a second central portion. The third end and the fourth end extend through the third orifice and the fourth orifice. The third end and the fourth end are configured to contact pre-vapor formulation contained in the reservoir. The second central portion overlaps with the first central portion.

In at least one example embodiment, at least one of the wick and the second wick is generally U-shaped.

In at least one example embodiment, the housing is formed of plastic.

In at least one example embodiment, the sidewall has a first outer diameter at the first end and a second outer diameter at the second end. The first outer diameter is larger than the second outer diameter.

In at least one example embodiment, the second housing is configured to receive a portion of the cartridge therein, such that the central portion of the wick contacts the heater.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION OF EXAMPLE EMBODIMENTS

Figure 1:
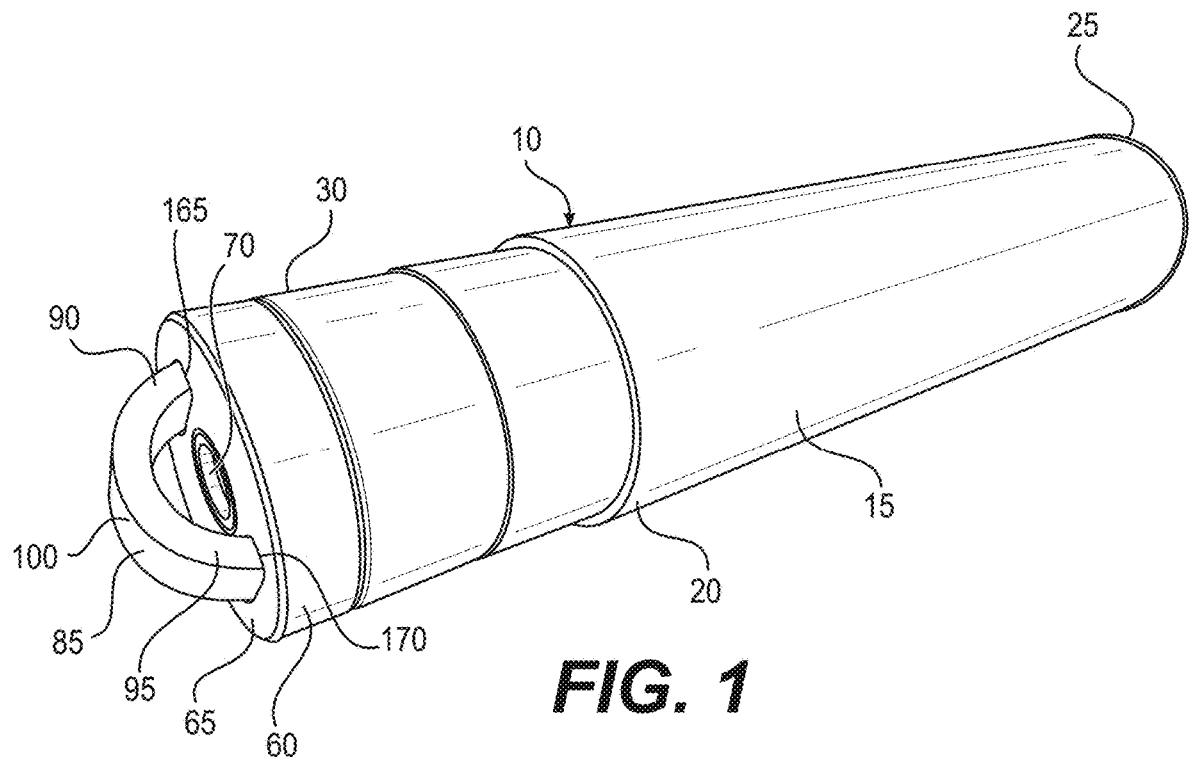
FIG. 1 is a perspective view of a second end of an end cap on a cartridge according to at least one example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

At least one example embodiment relates to a cartridge of an electronic vaping device.

FIG. 1 is a perspective view of a cartridge according to at least one example embodiment.

Figure 2:
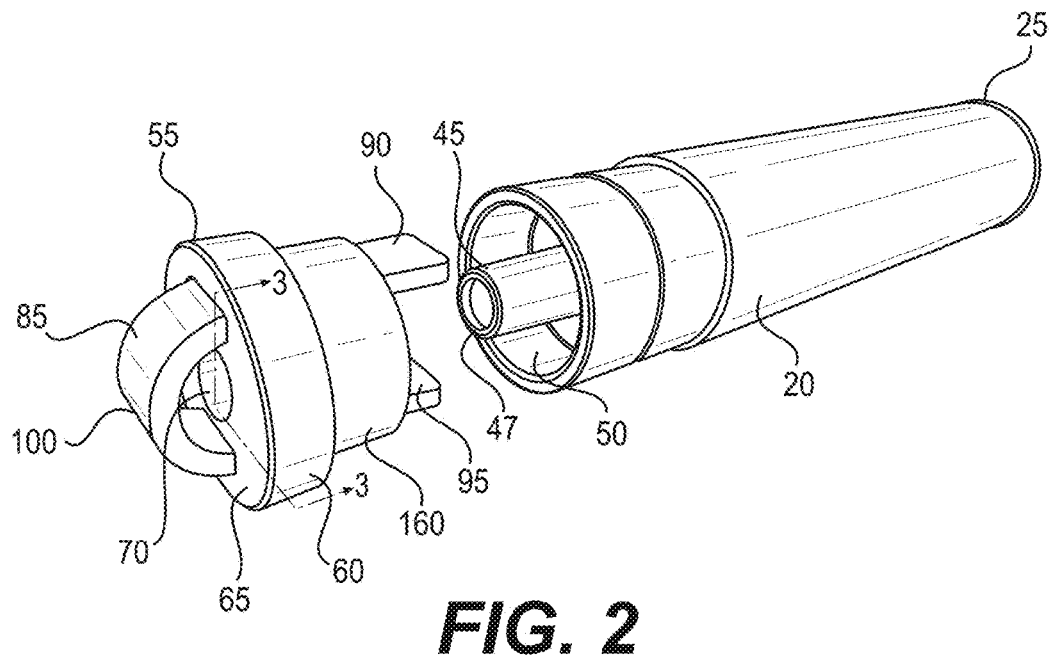
FIG. 2 is an exploded view of an end cap and a cartridge according to at least one example embodiment.

FIG. 2 is an exploded view of an end cap and a cartridge according to at least one example embodiment.

In at least one example embodiment, as shown in FIGS. 1 and 2, a cartridge 10 includes a housing 15 extending in a longitudinal direction. In at least one example embodiment, the housing 15 includes a sidewall 20. The housing 15 has a first end 25 and a second end 30. In at least one example embodiment, the cartridge 10 is a single piece that may be molded and/or 3D printed.

In at least one example embodiment, the housing 15 may have a generally cylindrical cross-section. In other example embodiments, the housing 15 may have a generally triangular cross-section and/or an inner and/or outer diameter of the housing 15 may vary along a length thereof. In some example embodiments, as shown in FIG. 1, the housing 15 may have a greater diameter at the first end 25 than at the second end 30.

In at least one example embodiment, the cartridge 10 also includes an end cap 55. The end cap 55 includes an end cap sidewall 60 and an end wall 65. The end cap sidewall 60 is generally cylindrical and has generally a same diameter as a diameter of the second end 30 of the housing 15.

In at least one example embodiment, the end cap sidewall 60 includes a portion 160 (shown in FIG. 2) having a smaller outer diameter than an inner diameter of the housing 15 at the second end 30. Thus, a portion of the end cap sidewall 60 may be received within the second end 30 of the housing 15. The portion 160 of the end cap sidewall 60 may be held in place within the second end 30 of the housing 15 by friction fit, snap fit, or any other suitable connection. For example, an adhesive may be used to hold the portion 160 of the end cap sidewall 60 in the housing 15. Alternatively, the portion 160 of the end cap sidewall 60 and the second end 30 of the housing 15 may include threaded portions that provide a threaded connection between the end cap 55 and the housing 15.

In at least one example embodiment, the end cap 55 includes at least one inlet 70 therein. The at least one inlet 70 is in communication with an air passage 47 defined by an inner tube 45 (as discussed below with respect to FIG. 2).

In at least one example embodiment, the end cap 55 also includes a first orifice 165 and a second orifice 170 extending through the end cap end wall 65.

In at least one example embodiment, the cartridge 10 also includes a wick 85. The wick 85 includes a first end 90, a second end 95, and a central portion 100. The first end 90 and the second end 95 extend through first orifice 165 and the second orifice 175 of the end cap 55, respectively. The first end 90 and the second end 95 are configured to contact pre-vapor formulation contained in a reservoir 50. The central portion 100 of the wick 85 extends over the at least one inlet 70. In at least one example embodiment, the wick 85 is formed of at least one of a cellulosic material, a glass material, glass fibers, and cotton. In at least one example embodiment, the wick may be formed of cellulose filter paper having a thickness ranging from about 0.6 mm to about 1.0 mm.

In at least one example embodiment, the wick 85 may include filaments (or threads) having a capacity to draw the pre-vapor formulation. For example, the wick 85 may be a bundle of glass (or ceramic) filaments, a bundle including a group of windings of glass filaments, etc., all of which arrangements may be capable of drawing pre-vapor formulation via capillary action by interstitial spacings between the filaments. In at least one example embodiment, the wick 85 may include one to eight filament strands, each strand comprising a plurality of glass filaments twisted together. The filaments may have a cross-section that is generally cross-shaped, clover-shaped, Y-shaped, or in any other suitable shape.

In at least one example embodiment, the wick 85 may include any suitable material or combination of materials. Examples of suitable materials may be, but not limited to, glass, ceramic- or graphite-based materials. The wick 85 may have any suitable capillarity drawing action to accommodate pre-vapor formulations having different physical properties such as density, viscosity, surface tension and vapor pressure.

In at least one example embodiment, the wick 85 is generally U-shaped.

In at least one example embodiment, the housing 15 and end cap 55 are formed of plastic. The housing 15 and end cap 55 may be injection molded or 3D printed. The plastic may be clear, tinted, and/or colored plastics.

In at least one example embodiment, as shown in FIG. 2, the inner tube 45 is integrally formed with the housing 15 and is coaxially positioned within the housing 15. The reservoir 50 is defined between an outer surface of the inner tube 45 and an inner surface of the housing 15. The reservoir 50 is sized and configured to contain a pre-vapor formulation.

In at least one example embodiment, the inner tube 45 is integrally formed with the housing 15. The inner tube 45 extends in the longitudinal direction. The inner tube 45 communicates with at least one outlet 40 (shown in FIGS. 3 and 4).

In at least one example embodiment, the pre-vapor formulation is a material or combination of materials that may be transformed into a vapor. For example, the pre-vapor formulation may be a liquid, solid and/or gel formulation including, but not limited to, water, beads, solvents, active ingredients, ethanol, plant extracts, natural or artificial flavors, and/or vapor formers such as glycerin and propylene glycol.

In at least one example embodiment, the cartridge 10 may be replaceable. In other words, once the pre-vapor formulation of the cartridge 10 is depleted, the cartridge 10 may be discarded and replaced with a new cartridge. In another example embodiment, the reservoir 50 in the cartridge 10 may be refilled, such that the cartridge 10 is reusable.

In at least one example embodiment, the reservoir 50 may optionally contain a storage medium (not shown). The storage medium is configured to store the pre-vapor formulation therein. The storage medium 210 may include a winding of cotton gauze or other fibrous material.

In at least one example embodiment, the storage medium may be a fibrous material including at least one of cotton, polyethylene, polyester, rayon and combinations thereof. The fibers may have a diameter ranging in size from about 6 microns to about 15 microns (e.g., about 8 microns to about 12 microns or about 9 microns to about 11 microns). The storage medium may be a sintered, porous or foamed material. Also, the fibers may be sized to be irrespirable and may have a cross-section which has a Y-shape, cross shape, clover shape or any other suitable shape.

Figure 3:
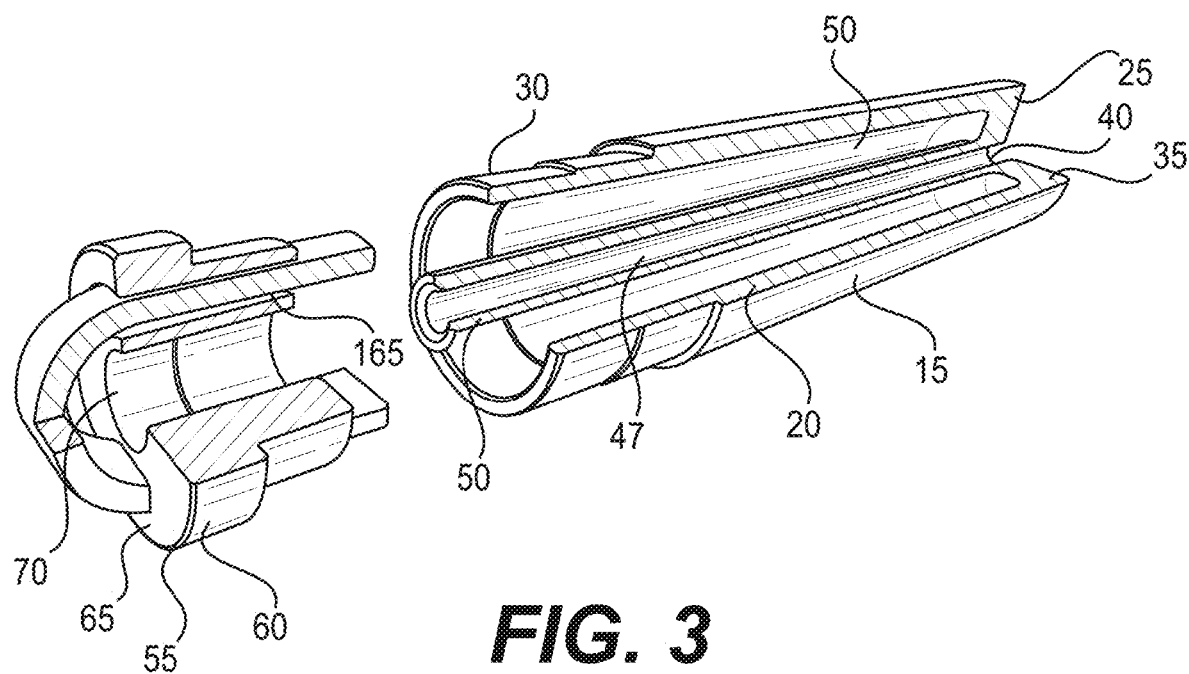
FIG. 3 is an exploded, cross-sectional view of the cartridge of FIG. 2 along line III-III according to at least one example embodiment.

FIG. 3 is an exploded, cross-sectional view of the cartridge of FIG. 2 along line III-III according to at least one example embodiment.

In at least one example embodiment, as shown in FIG. 3, the cartridge 10 is the same as shown in FIGS. 1 and 2. As shown in FIG. 3, the housing 15 includes a transverse end wall 35 at a first end 25 of the housing 15. The transverse end wall 35 is integrally formed with the sidewall 20 and the inner tube 45. The transverse end wall 35 includes at least one outlet 40 therein. The at least one outlet 40 is in communication with an air passage 47 defined by the inner tube 45.

Figure 4:
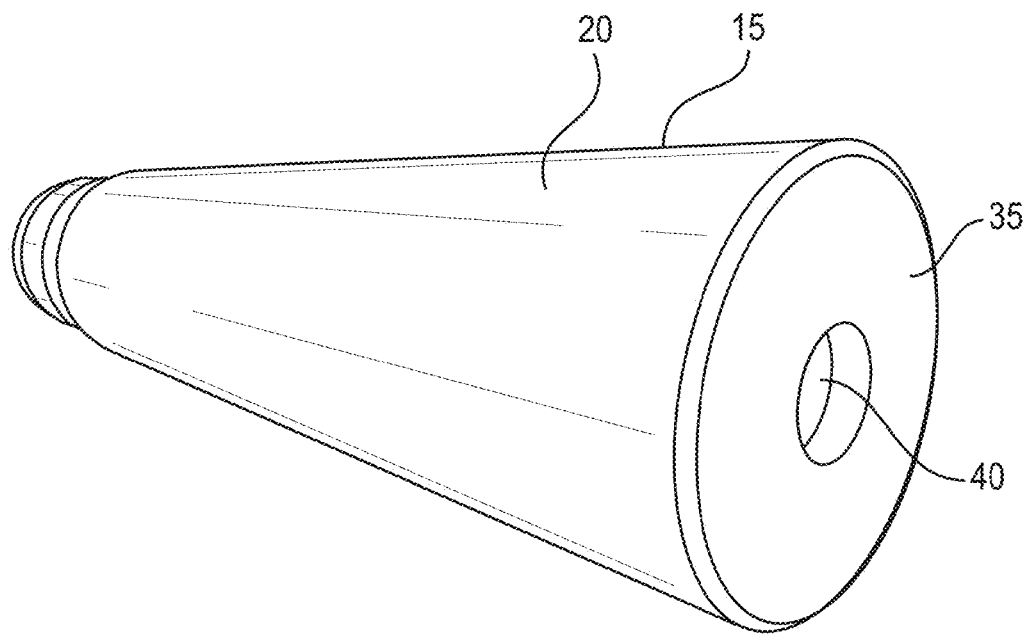
FIG. 4 is a perspective view of a cartridge according to at least one example embodiment.

FIG. 4 is a perspective view of another end of the cartridge according to at least one example embodiment.

In at least one example embodiment, as shown in FIG. 4, the cartridge 10 is the same as in FIGS. 1, 2, and 3. As shown in FIG. 4, the transverse end wall 35 has a generally planar surface. In other example embodiments, the transverse end wall 35 may be convex or concave.

Figure 5:
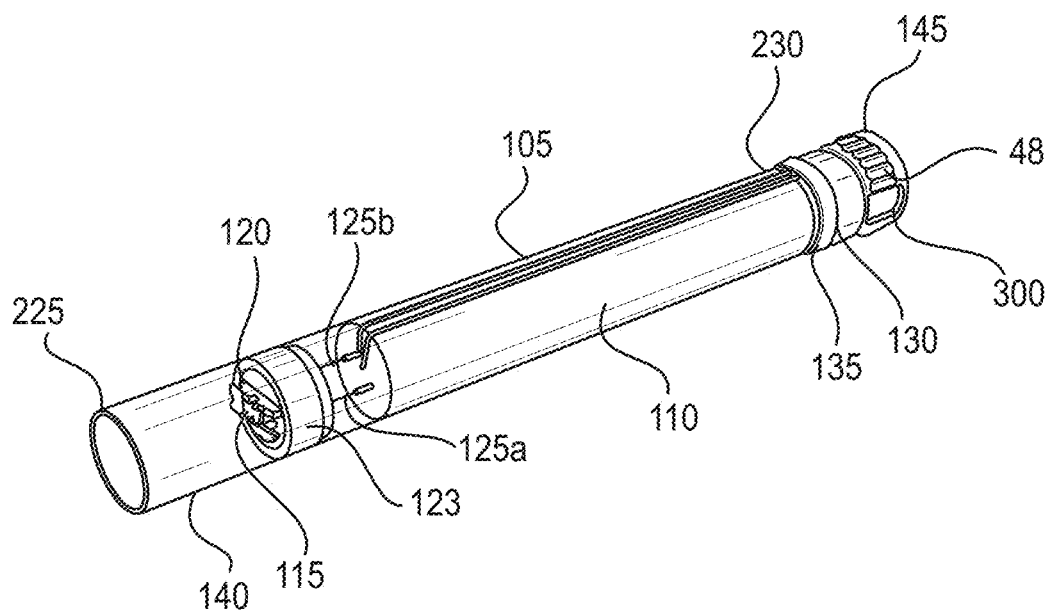
FIG. 5 is a perspective view of a power supply section according to at least one example embodiment.

FIG. 5 is a perspective view of a power supply section according to at least one example embodiment.

In at least one example embodiment, as shown in FIG. 5, a power supply section 105 includes a housing 140 extending in a longitudinal direction. The housing 140 is shown transparent for purposes of illustration only. The housing 140 has a first housing end 225 and a second housing end 230. The first housing end 225 is configured to receive at least a portion of the cartridge 10 therein.

In at least one example embodiment, the power supply section 105 includes a heater 115 and a battery 110. The heater 115 may be a planar heater or a wire coil heater.

In at least one example embodiment, the heater 115 may be formed of any suitable electrically resistive materials. Examples of suitable electrically resistive materials may include, but not limited to, titanium, zirconium, tantalum and metals from the platinum group. Examples of suitable metal alloys include, but not limited to, stainless steel, nickel, cobalt, chromium, aluminum-titanium-zirconium, hafnium, niobium, molybdenum, tantalum, tungsten, tin, gallium, manganese and iron-containing alloys, and super-alloys based on nickel, iron, cobalt, stainless steel. For example, the heater 115 may be formed of nickel aluminide, a material with a layer of alumina on the surface, iron aluminide and other composite materials, the electrically resistive material may optionally be embedded in, encapsulated or coated with an insulating material or vice-versa, depending on the kinetics of energy transfer and the external physicochemical properties required. The heater 115 may include at least one material selected from the group consisting of stainless steel, copper, copper alloys, nickel-chromium alloys, super alloys and combinations thereof. In an example embodiment, the heater 115 may be formed of nickel-chromium alloys or iron-chromium alloys. In another example embodiment, the heater 115 may include a layer of a ceramic or alumina having an electrically resistive layer on an outside surface thereof, such as a layer of platinum. In at least one example embodiment, the heater 115 may include at least one of ceramic, alumina, or zirconia.

In at least one example embodiment, the heater 115 has dimensions ranging from about 0.25 mm to about 5.0 mm. At least two electrical leads 125a, 125b may extend from the heater 115 and electrically connect the heater 115 to the battery 110. The electrical leads may be formed of nickel. The heater 115 may have an electrical resistance of about 2.6 ohms at 25° C. and an electrical resistance of about 5.6 ohms at 350° C.

In at least one example embodiment, the heater 115 has a width and/or length that is less than a width and/or length of the wick 85 at a point where the heater 115 contacts the wick 85. Thus, when the heater 115 contacts the wick 85, a surface of the heater 115 fully contacts the wick 85 and a portion of the wick 85 extends beyond borders of the heater 115. The heater 115 may heat pre-vapor formulation in the wick 85 by thermal conduction. Alternatively, heat from the heater 115 may be conducted to the pre-vapor formulation by means of a heat conductive element or the heater 115 may transfer heat to the incoming ambient air that is drawn through the electronic vaping device 200 during vaping, which in turn heats the pre-vapor formulation by convection.

As shown in FIG. 5, the heater 115 may be supported by a support 120 that is surrounded at least in part by an insulation sleeve 123.

In at least one example embodiment, the battery 110 may be a Lithium-ion battery or one of its variants, for example a Lithium-ion polymer battery. Alternatively, the battery 110 may be a nickel-metal hydride battery, a nickel cadmium battery, a lithium-manganese battery, a lithium-cobalt battery or a fuel cell.

In at least one example embodiment, the battery 110 may be rechargeable and may include circuitry configured to allow the battery 110 to be chargeable by an external charging device.

In at least one example embodiment, the power supply section 105 may also include a control circuit 135 and a sensor 130.

In at least one example embodiment, the sensor 130 is a sensor that is configured to sense an air pressure drop. The sensor 130 may be a microelectromechanical (MEMS) sensor. The control circuit 135 may initiate application of voltage from the battery 110 to the heater 115 when negative pressure is sensed by the sensor 130.

In at least one example embodiment, the power supply section 105 may include a heater activation light 48 in and/or adjacent a power supply end cap 145 of the power supply section 105. The control circuit 135 may be configured to initiate lighting of the heater activation light 48 when the heater 115 is activated. The heater activation light 48 may include a light-emitting diode (LED). Moreover, the heater activation light 48 may be arranged to be visible to an adult vaper. In addition, the heater activation light 48 may indicate e-vaping system diagnostics and/or indicate that recharging is in progress. The heater activation light 48 may also be configured such that the adult vaper may activate and/or deactivate the heater activation light 48 for privacy.

In at least one example embodiment, at least one air inlet 300 may be located adjacent the power supply end cap 145. The at least one air inlet 300 may extend through the housing 140.

In at least one example embodiment, the control circuit 135 may supply power to the heater 115 responsive to the sensor 130. In one example embodiment, the control circuit 135 may include a maximum, time-period limiter. In another example embodiment, the control circuit 135 may include a manually operable switch for an adult vaper to initiate a puff. The time-period of the electric current supply to the heater 115 may be pre-set depending on the amount of pre-vapor formulation desired to be vaporized. In yet another example embodiment, the control circuit 135 may supply power to the heater 115 as long as the sensor 130 detects a pressure drop.

When activated, the heater 115 may heat a portion of the wick 85 adjacent to and/or touching the heater 115 for less than about 10 seconds or less than about 5 seconds.

Figure 6:
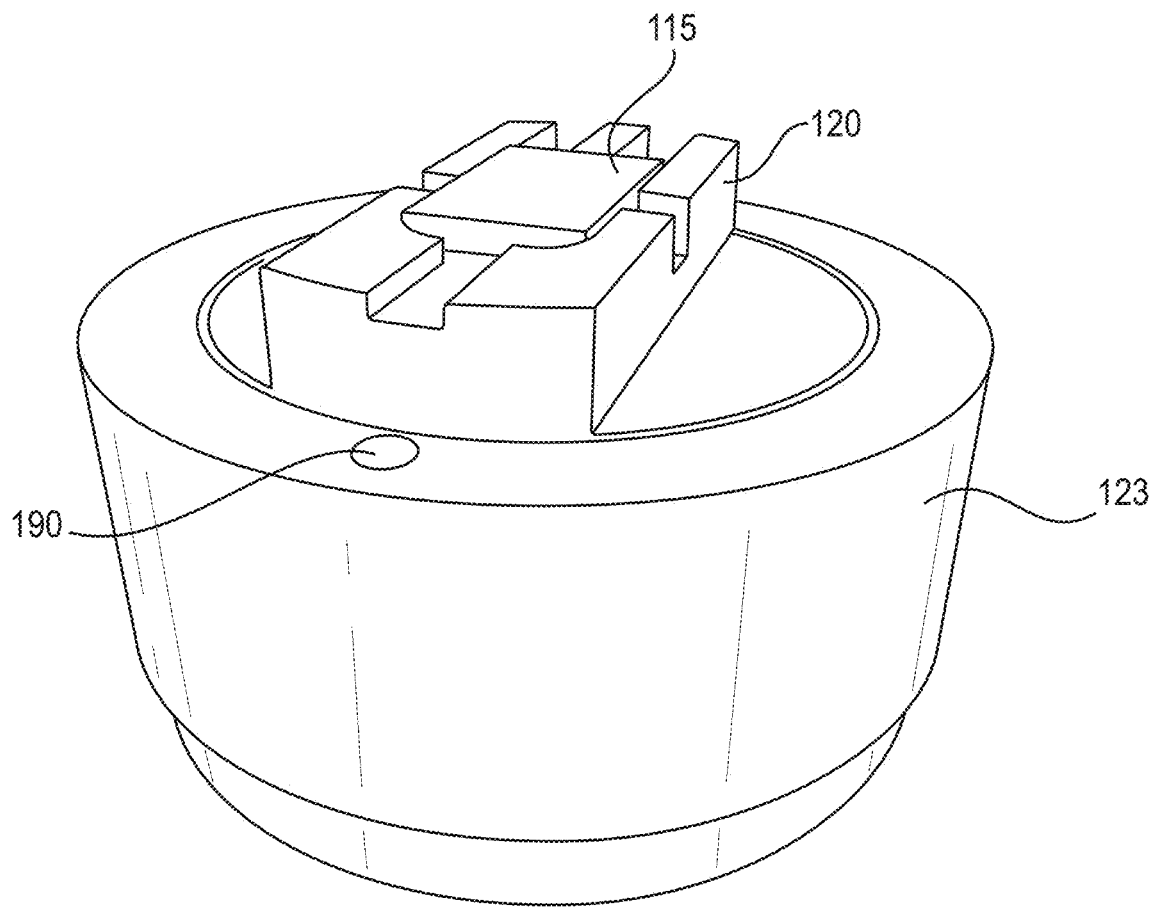
FIG. 6 is an enlarged, perspective view of a heater assembly according to at least one example embodiment.

FIG. 6 is an enlarged, perspective view of a heater assembly according to at least one example embodiment.

In at least one example embodiment, as shown in FIG. 6, as described with respect to FIG. 5, the heater 115 may be supported by the support 120 that is surrounded at least by the insulation sleeve 123. At least one through-hole 190 may extend through the insulation sleeve 123 to allow air to flow through the through-hole 190 to the air passage 47. The electrical leads 125a, 125b may also extend through respective through-holes 190 if desired. The support 120 may be generally rectangular in shape, and may include a depression sized and configured to receive the heater 115 therein. One or more channels may extend from the depression and electrical leads extending from the heater 115 may be positioned therein.

In at least one example embodiment, the insulation sleeve 123 is generally cylindrical and has an outer diameter that is about the same or less than an inner diameter of the housing 140. Thus, the insulation sleeve 123 may be held in place in the housing 140 by friction fit. In other example embodiments, the insulation sleeve 123 may be held in place by any suitable adhesive or mechanism.

At least one example embodiment relates to an electronic vaping device.

Figure 7:
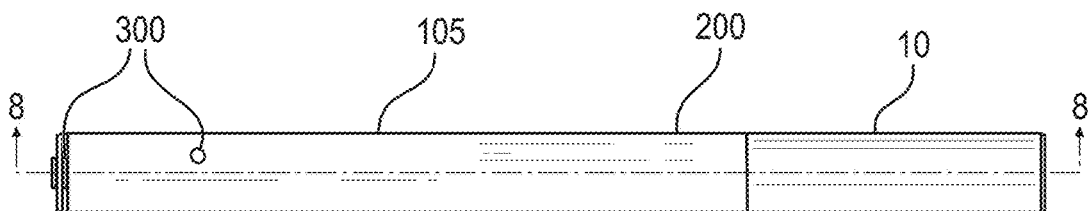
FIG. 7 is a side view of an electronic vaping device according to at least one example embodiment.

FIG. 7 is a side view of an electronic vaping device according to at least one example embodiment.

In at least one example embodiment, as shown in FIG. 7, an electronic vaping device 200 may include the cartridge 10 and the power supply section 105. In at least one example embodiment, an air inlet 300 may be located at the power supply end cap 145 or along the housing 140 of the power supply section 105.

In at least one example embodiment, the air inlets 300 may be machined into the housing 140 with precision tooling such that their diameters are closely controlled and replicated from one electronic vaping device 200 to the next during manufacture so as to control a resistance-to-draw of each electronic vaping device 200.

In at least one example embodiment, the electronic vaping device 200 may be about 80 mm to about 200 mm long and about 7 mm to about 15 mm in diameter. For example, in one example embodiment, the electronic vaping device may be about 84 mm long and may have a diameter of about 7.8 mm.

Figure 8:
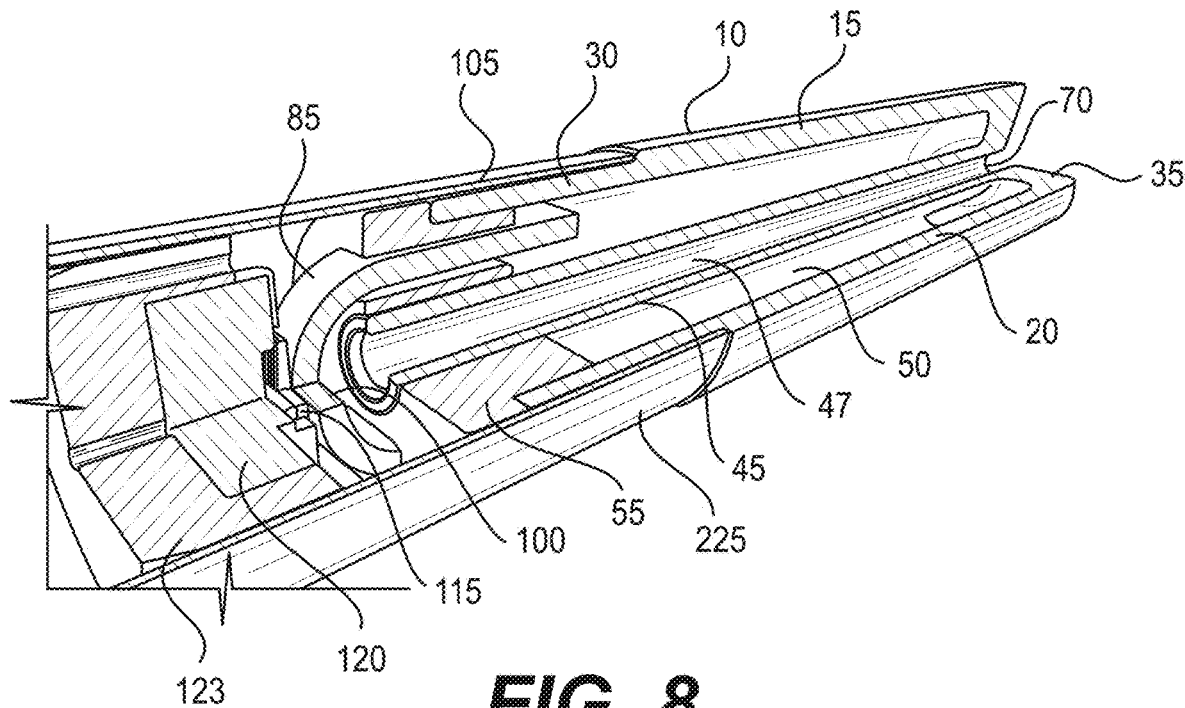
FIG. 8 is a perspective, cross-sectional view of a portion of the electronic vaping device of FIG. 7 along line VIII-VIII according to at least one example embodiment.

FIG. 8 is a perspective, cross-sectional view of a portion of the electronic vaping device of FIG. 7 according to at least one example embodiment.

In at least one example embodiment, as shown in FIG. 8, when the second end 30 of the cartridge 10 is inserted into the first end 225 of the housing 140 of the power supply section 105, the central portion 100 of the wick 85 contacts the heater 115. In at least one example embodiment, an entire surface of the heater 115 is in complete contact with the wick 85.

Figure 9:
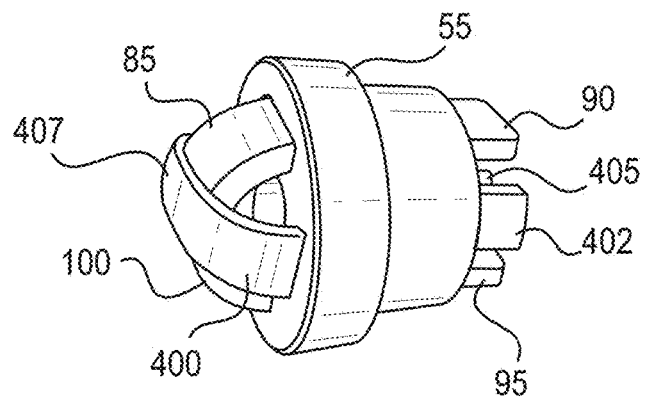
FIG. 9 is a perspective view of an end cap according to at least one example embodiment.

In at least one example embodiment, as shown in FIG. 9, instead of including an end cap 55 with a single wick, the end cap 55 may include a third orifice and fourth orifice that extend through the end cap and a second wick 400. The second wick includes a third end 402, a fourth end 405, and a second central portion 407. The third end 402 and the fourth end 405 extend through the third orifice and the fourth orifice. The third end 402 and the fourth end 405 are configured to contact pre-vapor formulation contained in the reservoir. The second central portion 407 overlaps with the first central portion 100 of the first wick 85.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

We claim:

1. A cartridge of an electronic vaping device, the cartridge comprising:
   a housing extending in a longitudinal direction, the housing including,
   a sidewall including a first end and a second end, and
   a transverse wall at the first end of the sidewall, the transverse wall including at least one outlet therein;
   a reservoir in the housing, the reservoir configured to contain a pre-vapor formulation;
   an end cap connected with the sidewall of the housing at the second end thereof, the end cap including,
   an end cap sidewall, and
   an end wall including a first orifice, a second orifice, a third orifice, and a fourth orifice extending therethrough, the first orifice and the second orifice in communication with the reservoir when the end cap sidewall is received in the sidewall of the housing;
   a first wick including a first end, a second end, and a first central portion, the first end and the second end respectively extending through the first orifice and the second orifice in the end wall of the end cap; and
   a second wick, the second wick including a third end, a fourth end, and a second central portion between the third end and the fourth end, the third end and the fourth end extending through the third orifice and the fourth orifice, the third end and the fourth end configured to contact pre-vapor formulation contained in the reservoir, the second central portion overlapping with the first central portion.

2. The cartridge of claim 1, further comprising:
   an inner tube within the sidewall, the inner tube extending in the longitudinal direction, and the inner tube in communication with the at least one outlet.

3. The cartridge of claim 2, wherein the sidewall and the end cap sidewall are cylindrical.

4. The cartridge of claim 3, wherein the end cap sidewall has a smaller outer diameter than an inner diameter of the sidewall of the housing, such that the end cap sidewall is configured to be received in the sidewall of the housing.

5. The cartridge of claim 4, wherein the end wall of the end cap includes at least one inlet therein, the at least one inlet in communication with the inner tube when the end cap sidewall is received in the sidewall of the housing.

6. The cartridge of claim 5, wherein the first central portion of the first wick extends over the at least one inlet.

7. The cartridge of claim 1, wherein the first wick is formed of a cellulosic material, a glass material, glass fibers, cotton, or any combination thereof.

8. The cartridge of claim 1, wherein at least one of the first wick and the second wick is U-shaped.

9. The cartridge of claim 1, wherein the housing is formed of plastic.

10. An electronic vaping device comprising:
a cartridge including,
a first housing extending in a longitudinal direction, the first housing including,
a sidewall including a first end and a second end, and
a transverse wall at the first end of the sidewall, the transverse wall including at least one outlet therein,
a reservoir in the first housing, the reservoir configured to contain a pre-vapor formulation,
an end cap connected with the sidewall of the first housing at the second end thereof, the end cap including,
an end cap sidewall, and
an end wall including a first orifice, a second orifice, a third orifice, and fourth orifice extending therethrough, the first orifice and the second orifice in communication with the reservoir when the end cap sidewall is received in the sidewall of the first housing,
a first wick including a first end, a second end, and a first central portion, the first end and the second end respectively extending through the first orifice and the second orifice in the end wall of the end cap,
a second wick, the second wick including a third end, a fourth end, and a second central portion between the third end and the fourth end, the third end and the fourth end extending through the third orifice and the fourth orifice, the third end and the fourth end configured to contact pre-vapor formulation contained in the reservoir, the second central portion overlapping with the first central portion; and
a power supply section including,
a second housing extending in the longitudinal direction, the second housing configured to connect with the first housing via a connection,
a battery in the second housing,
a heater electrically connected to the battery, and
a support configured to support the heater.

11. The electronic vaping device of claim 10, wherein the support is ceramic.

12. The electronic vaping device of claim 10, further comprising:
an insulation sleeve adjacent the support.

13. The electronic vaping device of claim 10, wherein the cartridge further comprises:
an inner tube within the sidewall, the inner tube extending in the longitudinal direction, and the inner tube in communication with the at least one outlet.

14. The electronic vaping device of claim 13, wherein the sidewall and the end cap sidewall are cylindrical.

15. The electronic vaping device of claim 14, wherein the end cap sidewall has a smaller outer diameter than an inner diameter of the sidewall of the first housing, such that the end cap sidewall is configured to be received in the sidewall of the first housing.

16. The electronic vaping device of claim 15, wherein the end wall of the end cap includes at least one inlet therein, the at least one inlet in communication with the inner tube when the end cap sidewall is received in the sidewall of the first housing.

* * * * *